US005654144A

United States Patent [19]

Mann et al.

[11] Patent Number: 5,654,144

[45] Date of Patent: Aug. 5, 1997

[54] DETECTION OF YERSINIA USING THE POLYMERASE CHAIN REACTION

[75] Inventors: Barbara J. Mann, Charlottesville, Va.; Sheila J. Wood, Edgewood, Md.

[73] Assignee: The United States of America as represented by the Secretary of the Army, Washington, D.C.

[21] Appl. No.: 433,551

[22] Filed: Apr. 24, 1995

[51] Int. Cl.$^6$ .............................. C12Q 1/68; C12P 19/34; C07H 21/04

[52] U.S. Cl. ............................ 435/6; 435/91.2; 435/810; 536/24.32; 536/24.33; 935/8; 935/78; 204/456; 204/606

[58] Field of Search ................................ 435/6, 912, 810; 536/24.32, 24.33; 935/8, 77, 78

[56] References Cited

PUBLICATIONS

Barry, T. et al., "The 16s/23s Ribosomal Spacer Region as a Target for DNA Probes to identify Eubacteria," PCR Methods and Applications 1:51–56, 1991.

Weisburg, W.G. et al., "16S Ribosomal DNA Amplification for Phylogenetic Study," Journal of Bacteriology, vol. 173, No. 2, pp. 697–703, Jan. 1991.

Robins–Brown, R. et al., "Evaluation of DNA Colony Hybridization and Other Techniques for Detection of Virulence in Yersinia Species," Journal of Clinical Microbiology, vol. 27, No. 4 pp. 644–650, 1989.

Ibrahim, A., "Polymerase Chain Reaction–Gene Probe Detection System Specific for Pathogenic Strains of Yersinia enterocolitica," Journal of Clinical Microbiology, vol. 30, No. 8, pp. 1942–1947, Aug. 1992.

Feng, Peter, "Identification of invasive Yersinia species using oligonucleotide probes," Molecular and Cellular Probes, 6, pp. 291–297, 1992.

Kapperud, G., et al, "A Synthetic Oligonucleotide Probe and a Cloned Polynucleotide Probe Based on the yopA Gene for Detection and Enumeration of Virulent Yersinia enterocolitica," Applied and Evironmental Microbiology, vol. 56, No. 1, pp. 17–23, Jan. 1990.

Schoerner, C, et al., "Differentiation of Serological Responses to Yersinia enterocolitica Serotype 09 and Brucella Species by Immunoblot or Enzyme–Linked Immunosorbent Assay Using Whole Bacteria and Yersinia Outer Membrane Proteins," vol. 28, No. 7, pp. 1570–1574, Jul. 1990.

Kwaga, J., et al., "Detection of Pathogenic Yersinia enterocolitica by Polymerase Chain Reaction and Digoxigenin–Labled Polynucleotide Probes," Journal of Clinical Microbiology, vol. 30, No. 10., pp. 2668–2673, Oct. 1992.

Gobel, U., et al, "Oligonucleotide probes complementary to variable regions of ribosomal BNA discriminate between Mycoplasma species" J Gen Microbiol. 133, 1969–1974.

Andersen, J.K., et al, "Epidemiological typing of Yersinia enterocolitica by analysis of restriction fragment length polymorphisms with a cloned ribosomal RNA gene," J. Med Microbiol., vol. 32, pp. 179–187, 1990.

Clark, C., et al., "The Laredo strain and other Entamoeba histolytica–like' amoebae are Entamoeba moshkovskii", Molecular and Biochemical Parasitology, 46, pp. 11–18, 1991.

Schmidt, Methods in Molecular and Cellular Biology (1994) 5.3–12.

Schoerner et al, Journal of Clinical Microbiology (1990) 28:1570–1574.

*Primary Examiner*—W. Gary Jones
*Assistant Examiner*—Carla Myers
*Attorney, Agent, or Firm*—Ulysses John Biffon; Edward L. Stolarum

[57] ABSTRACT

A novel laboratory method and a kit for rapid detection and identification of Yersinia bacteria using the polymerase chain reaction with specific primers and specific restriction enzymes to differentiate among Yersinia at the species level and to separate Yersinia from other species of bacteria.

10 Claims, 2 Drawing Sheets

M- Lambda DNA cut with HindIII= molecular weight markers
Ent- Yersinia entercolitica
Fred- Yersinia fredriksenii
Int- Yersinia intermedia
Kris- Yersinia kristensenii
Pestis- Yersinia pestis
Pseudo- Yersinia pseudotuberculosis
Sal- Salmonella thyphimurium
Coli- Escherichia coli
0- no DNA

M- Lambda DNA cut with HindIII= molecular weight markers
Ent- Yersinia entercolitica
Fred- Yersinia fredriksenii
Int- Yersinia intermedia
Kris- Yersinia kristensenii
Pestis- Yersinia pestis
Pseudo- Yersinia pseudotuberculosis
Sal- Salmonella thyphimurium
Coli- Escherichia coli
0- no DNA

M- Lambda DNA cut with HindIII= molecular weight markers
Ent- Yersinia entercolitica
Pestis- Yersinia pestis
Pseudo- Yersinia pseudotuberculosis
Numbers 2 thru 9- Yersinia enterocolitica, different strains

DETECTION OF YERSINIA USING THE POLYMERASE CHAIN REACTION

GOVERNMENT INTEREST

The invention described herein may be manufactured, licensed, and used by or for the U.S. Government.

BACKGROUND OF THE INVENTION

1. Field of the Invention

This invention relates to a method and a kit for the rapid detection of pathogenic organisms in environmental samples using the polymerase chain reaction. More specifically, it relates to methods for differentiating among various species of pathogenic and non-pathogenic Yersinia bacteria by specific restriction enzymes in conjunction with the polymerase chain reaction.

2. Description of the Prior Art

Bacterial contamination of food, water, or soil can result in serious illness in humans and animals. Detection and identification of pathogenic organisms are important for monitoring unwarranted biological attacks, for containment of potential epidemics, for elimination of natural host reservoirs, for prevention of further contamination, and for appropriate subsequent treatment should exposure occur. Rapid detection and identification of the sources of contamination provides the information to properly eliminate and prevent the spread of bacteria so as to ensure the quality and safety of food and water resources, and the prevention of epidemics or biological attacks. The polymerase chain reaction, herein referred to as PCR, is an in-vitro method of amplifying DNA sequences. Target DNA from bacterial, viral, fungal, parasitic or biological source of interest, may be amplified and detected in minute quantities, theoretically as small as one molecule. Practical applications have used 100 organisms, or the equivalent of 10 nanograms of DNA, for successful identification. The target DNA to be amplified must be flanked by a known sequence of several nucleotides; short pieces of DNA are synthesized with sequences identical to the known sequences; these are referred to as oligonucleotide primers.

At present, there is no known methodology for identifying Yersinia bacterial species using restriction enzymes in conjunction with PCR. There is a need, therefore, for a rapid and convenient method for identifying such bacteria.

The PCR process in accordance with this invention requires denaturing the target DNA strand into two separate strands by heating it to 93–96 degrees C., preferably 95 degrees C. A predetermined primer is then annealed to each of the separate strands at the flanking positions at 37–60 degrees C., preferably 55 degrees C. A heat-resistant enzyme, referred to as Taq polymerase, synthesizes a strand of DNA complementary to the existing DNA strands to form two complete double DNA copies of the original starting target DNA. By repeating this process once, four double-stranded chains are formed. Every time the process is repeated, the amount of PCR product is exponentially increased. The conditions of the PCR process may be slightly different, depending on the primers and DNA template used.

Electrophoresis is used to display patterns that differentiate between the DNAs of different genera of the bacteria in the sample. A restriction enzyme is added to the PCR product to generate an electrophoresis pattern specific to the individual species of bacteria.

SUMMARY OF THE INVENTION

This invention relates to a novel biological detection method for identifying bacteria of the Yersinia species, which comprises:

(a) adding a DNA template, a target DNA of Yersinia whose species is to be identified, to a mixture of a pair of primers wherein one member of the pair of primers is fd2 (SEQ. ID No. 1) or f16s (SEQ ID No. 2), and the other member of the pair of primers is r23s (SEQ ID No. 3) or Yer1 (SEQ. ID No. 4); a predetermined buffer solution; nucleotides including dATP, dTTP, dGTP, and dCTP; and a thermostable (enzyme) DNA polymerase;

(b) effecting the polymerase chain reaction followed by sequential incubations at a predetermined temperature for a predetermined time;

(c) digesting the resulting PCR product of a. with a restriction enzyme selected from the group consisting of Alu I, Hae III, MBOl, Ddel, Hinfl and a mixture thereof, and (d) electrophoresing the digested product of step (c) on agarose gel, whereby digestion patterns characterizing the species are displayed.

The method may comprise separate test runs with a blank, that is without DNA template, *E. coli*, or another known Yersinia as control.

A new biological detection kit for identifying Yersinia species using the process of this invention comprises the following:

(a) a PCR reagent comprising a predetermined buffer solution; a pair of primers wherein one member of the pair of primers is fd2 (SEQ. ID No. 1) or f16s (SEQ ID No. 2), and the other member of the pair of primers is r23s (SEQ ID No. 3) or Yer1 (SEQ ID No. 4); a thermostable DNA polymerase, selected from the group consisting of Taq. DNA polymerase, and native Taq; and nucleotides of dATP, dTTP, dGTP, and dCTP; for carrying out the polymerase chain reaction to amplify the DNA sequence of a sample of Yersinia to be added to the PCR reagent and to be identified; and (b) a restriction enzyme selected from the group consisting of Alu I, Hae III, Mbol, Ddel, Hinfl and a mixture thereof is to be added to the PCR product and electrophoresed in an agarose gel, to break down the amplified Yersinia DNA into an electrophoresis pattern which characterizes the species of Yersinia.

Additionally, *Escherichia coli* (*E. coli*) and a known Yersinia DNA template may included in the kit as controls.

DESCRIPTION OF THE PREFERRED EMBODIMENT OF THE INVENTION

Figure 1:
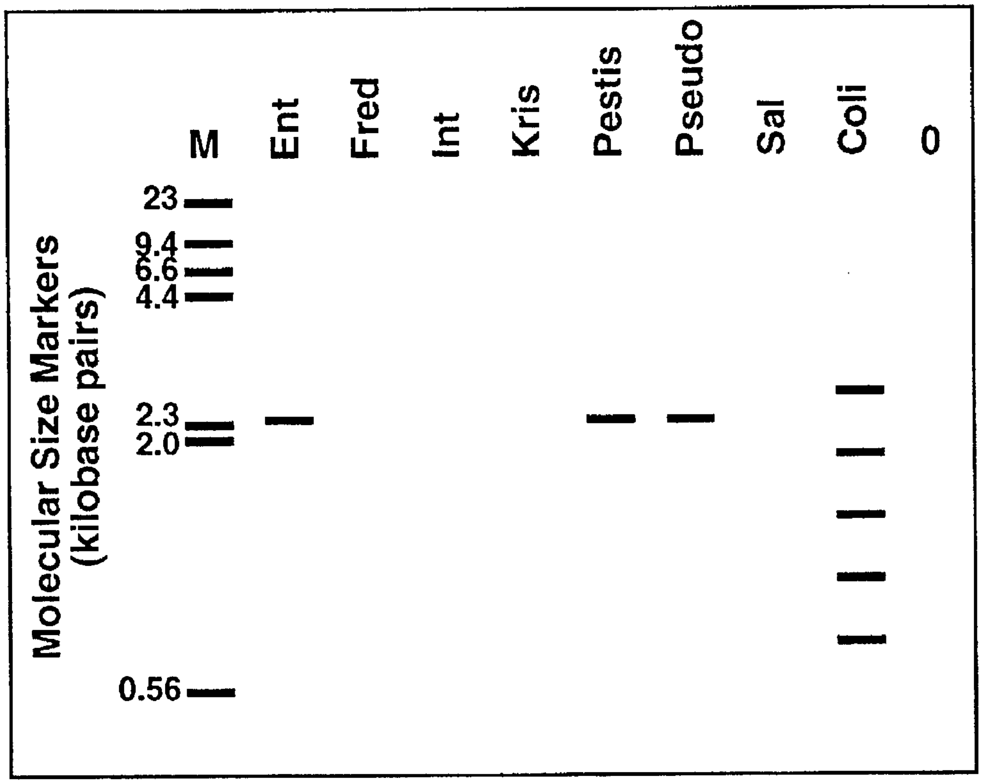
FIG. 1 is an electrophoretic pattern showing the PCR products produced from bacterial DNA template and primers Yer1 and f16s. PCR products are only produced from the three pathogenic species of Yersinia and have a molecular size of 2.4 kilobase (kb) pairs.

In the preferred embodiment of this invention, a set of four oligonucleotide primers are selected. They are as follows:

| Name | Sequence | Location | Source |
|---|---|---|---|
| fd2 | AGAGTTTGATCATGGCTC SEQ. ID. NO. 1 | nucleotide #8 in YEPRR16SA (Genbank Accession Number) | Genbank database |
| fl6s | TCGATGCAACGCGAAGAAA SEQ. ID. NO. 2 | nucleotide #3961 in YEPRR16SA (Genbank Accession Number) | Genbank database |
| r23s | AACGCTCCCCTACCCAAC SEQ. ID. NO. 3 reverse complement | nucleotide #34 in YEPRGGC (Genbank Accession Number) | Genbank database |
| Yerl | GTGATACGTTCGCTGCCG SEQ. ID. NO. 4 reverse complement | new sequence not in database | Mann |

Use of fd2 (SEQ. ID No. 1) for amplification of ribosomal RNA is described in Weisburg et al., "16S Ribosomal DNA Amplification for Phylogenetic Study," Journal of Bacteriology, Vol 173, No. 2, pp. 697–703, January 1991. (SEQ ID No: 1) Primers fd2 (SEQ ID No. 2) and r23s (SEQ ID No. 3) are used together to amplify most of the 16s gene and the region located between 16s and 23s; f16s and r23s (SEQ ID No. 3) are used together to amply a small part of the 16s gene, the region of DNA located between the 16s and 23s genes. (All the above genes have been deposited in the Genbank database.) The f16s (SEQ ID No. 2) and r23s (SEQ ID No. 3) primers are specifically selected by comparing the DNA sequences of 16s and 23s genes of Yersinia by Mann. Yer1 (SEQ ID No. 4) was selected from sequencing the intergene 16s-23s region by Mann.

Template DNA is prepared from a sample either of bacteria filtrate or bacterial culture, stored in 50% ethanol, pelleted and washed with phosphate buffer saline (PBS) and lysed by alkaline sodium dodecyl sulfate (alkaline SDS). Following are the bacteria in the sample:

*Yersinia enterocolitica* serotype 9

*Escherichia coli* (*E. coli*) MC 1061 (for control)

*Y. enterocolitica*-ATTC #23715

*Y. kristensenii*-ATTC #35669

*Y. frederiksenii*-ATTC #33641

*Y. intermedia*-ATTC #29909

One blank (without DNA for control)

The process of preparing the template DNA follows the method in the following reference: Barry et al., "The 16s/23s Ribosomal Spacer Region as a Target for DNA Probes to Identify Eubacteria," PCR Methods and Applications, 1:51–56, 1991. The text of this article on pages 52–53 is hereby incorporated by reference.

Among the above listed Yersinia bacteria, the first two Yersinia are pathogenic and the last three are non-pathogenic. The bacteria of either group give the same positive reactions. Therefore, a digestion process is needed to establish the identity of each species.

It is advisable to run a blank test using no DNA template and completing the test procedure as a control. An additional test run with bacteria such as *E. coli* or a known Yersinia species may be run as an additional control.

Yersinia bacteria, whether pathogenic or not, are thus quickly identified by species by the method and kit of this invention.

DNA polymerase, Taq, is purchased from Perkin Elmer Cetus. A native Taq polymerase or a cloned version is also acceptable.

Nucleotides and restriction enzymes are also purchased commercially.

It is to be understood that the kit contains the necessary ingredients for the PCR reactions to be carried out in a programmable PCR apparatus. The PCR product is then digested with a predetermined restriction enzyme included in the kit for differentiating among individual species of the Yersinia bacteria. The specific pattern is demonstrated by electrophoreses in an agarose gel.

EXAMPLE

PCR reactions were set up using primers fd2 (SEQ ID No. 1) and r23s (SEQ ID No. 3). The reaction vessel contained 50 picomoles of each of the primers, approximately 10 ng of template DNA (one Yersinia species at a time), 1× PCR buffer containing 10 mM Tris-HCl at pH 8.3, 50 mM MgCl2, 0.1% gelatin; 200 microM of each of the nucleotides, dATP, dTTP, dGTP, and dCTP; and 2.5 units of native Taq DNA polymerase in a total reaction volume of 50 microliter. The reactions were automatically carried out by the programmable PCR apparatus set at 95 degrees C. for five minutes followed by sequential incubations at 95 degrees C. for 1 minute for denaturing, 55 degrees C. for 1 minute for annealing, and 72 degrees C. for 1 minute for polymerizing. The process is repeated 30 times and followed by a 15 minute incubation period at 72 degrees C.

5 microliters of PCR product were loaded on 1% agarose gel and electrophoresed. A band of approximately 4 kb was visible in each lane. One reaction was run without any template DNA and no band was observed in this lane. Another reaction was run with *E. coli* DNA template for control. Electrophoresis at this stage is optional since it only verifies the PCR reaction was successful and does not identify the bacteria at the species or genus level. It will amplify *E. coli*, but not as well.

Digestion with restriction enzymes is carried out for the purpose of distinguishing among species. The PCR products are digested with restriction enzymes Alu I or Hae III. The digested products are electrophoresed on a 3 % agarose gel, which permits the separation of small DNA fragments and yields different fragment patterns which are characteristic of each species of Yersinia. The conditions of digestion were based on the instructions of the manufacturer of the restriction enzymes.

Figure 2:
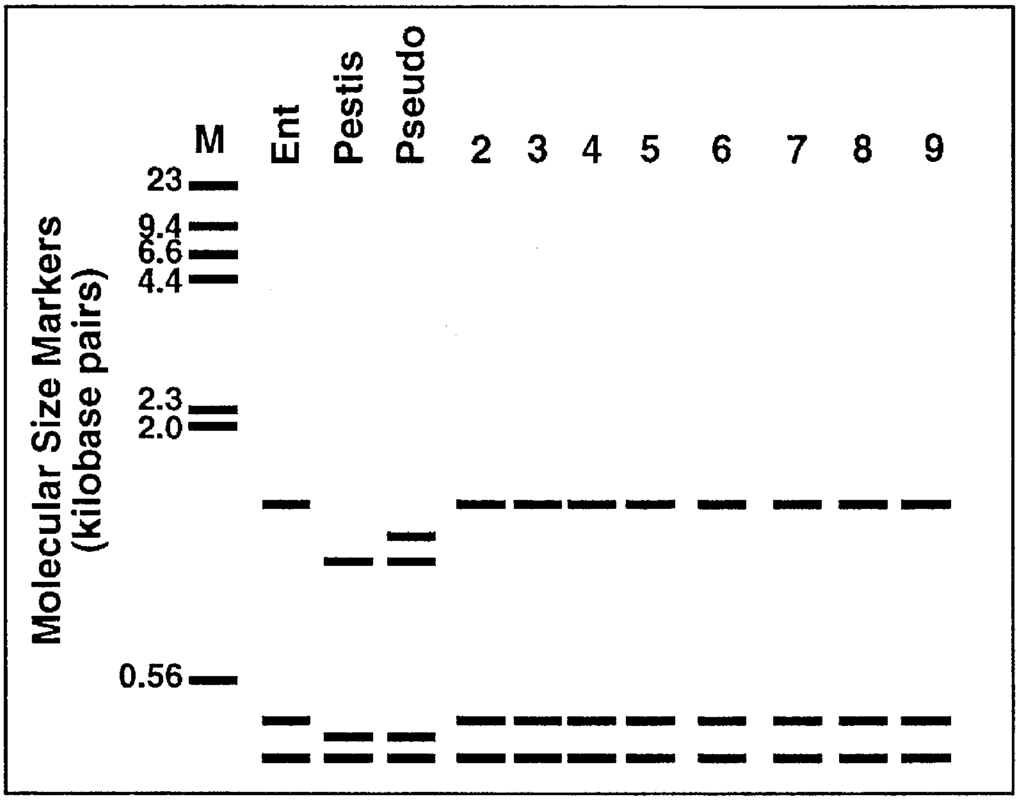
FIG. 2 shows the PCR products produced from bacterial DNA template and primers Yer1 and f16s followed by digestion with the enzyme AluI. Unique patterns are observed for each of the three pathogenic species of Yersinia thereby identifying them to the species level. In addition, identical patterns are shown for 8 different strains or isolates of *Yersinia enterocolitica* thereby specifically identifying this species.

The primer pair Yer1(SEQ. ID No. 4)-f16s (SEQ ID No. 2) was used to amplify the DNA located between the 16 23s rRNA genes of different Yersinia species. A PCR product was produced only with pathogenic species of Yersinia (FIG. 1). These products were digested with AluI. Digestion with AluI gave the same pattern with 8 different strains or isolates of *Yersinia enterocolitica*, thus specifically identifying this species (FIG. 2). In addition AluI digestion resulted in a specific and unique pattern for both *Yersinia pestis* and *Yersinia pseudotuberculosis* (FIG. 2), providing a means to specifically identify all three pathogenic species of Yersinia.

It is to be understood that the kit of this invention includes all necessary reagents for the PCR reaction, to be used with a programmable PCR apparatus and further includes the restriction enzymes. The process follows the method of this invention. After the PCR has been carried out and the PCR product has been digested with a specific restriction enzyme, the resulting digestion DNA fragments are electrophoresed as explained above.

The PCR process requires denaturing the target DNA strand into two separate strands by heating it to 93–96 degrees C., preferably 95 degrees C.; the primer is annealed to each of the separated strands at the flanking positions at 37–60 degrees C., preferably 55 degrees C.; and the polymerization chain reaction takes place at 72 degrees C.

It should be apparent that the embodiment described can be modified within the spirit and scope of the present invention. Thus, for example, the buffer solution may contain additional components, or lack certain components here specified. The scope of the present invention is not limited to the particular embodiment here described. Any such changes will be within the spirit and scope of the present invention as defined by the appended claims.

What is claimed is:

1. A method of identifying Yersinia species, comprising:

(a) introducing a DNA template isolated from Yersinia into a mixture of a pair of primers wherein one member of the pair of primers is fd2 (SEQ ID No. 1) or f16s (SEQ ID No. 2), and the other member of the pair of primers is r23s (SEQ ID No. 3) or Yer1 (SEQ ID No. 4), a buffer solution, nucleotides including dATP, dTTP, dGTP, and dCTP, and Taq DNA polymerase;

(b) performing PCR amplifying reactions;

(c) digesting the resulting PCR product of step (b) with a restriction enzyme selected from the group consisting of Alu I, Hae III, Mbol, Ddel, Hinfl, and a mixture thereof; and (d) electrophoresing the digested product of step (c) on a agarose gel which characterizes the digestion patterns thereby identifying the species.

2. The method of claim 1, further comprising introducing separately a known Yersinia DNA template as a positive control into a mixture of a pair of primers wherein one member of the pair of primers is fd2 (SEQ ID No. 1) or f16s (SEQ ID No. 2), and the other member of the pair of primers is r23s (SEQ ID No. 3) or Yer1 (SEQ ID No. 4), a buffer solution, nucleotides including dATP, dTTP, dGTP, and dCTP, and Taq DNA polymerase and repeating steps (b), (c), and (d).

3. The method of claim 1, further comprising separately adding sterilized water as a blank into a mixture of a pair of primers wherein one member of the pair of primers is fd2 (SEQ ID No. 1) or f16s (SEQ ID No. 2), and the other member of the pair of primers is r23s (SEQ ID No.3) or Yer1 (SEQ ID No. 4), a buffer solution, nucleotides including dATP, dTTP, dGTP, and dCTP; Taq DNA polymerase, and carrying out steps (b), (c), and (d).

4. The method of claim 1, wherein said performing the PCR includes heating the mixture to 93–96 degrees C. for 5 minutes, followed by sequentially incubating at 93–96 degrees C. for 1 minute, at 37–60 degrees C. for 1 minute, and 72 degrees C. for 1 minute, and repeating the foregoing steps about thirty times, followed by incubating at 72 degrees C. for 15 minutes.

5. The method of claim 1, where said performing PCR includes heating the mixture preferably to 95 degrees C. for 5 minutes, followed by sequentially incubating at 95 degrees C. for 1 minute, 52–55 degrees C. for 1 minute, and 72 degrees C. for 1 minute, and repeating the foregoing steps about thirty times.

6. The method of claim 1, wherein said performing the PCR reactions takes place in a programmable PCR apparatus.

7. The method of claim 1, wherein the agarose is 3% NuSieve.

8. A biological detection kit for identifying the species of Yersinia bacteria, comprising:

(a) a PCR reagent which comprises a buffer solution;

(b) a pair of primers wherein one member of the pair of primers is fd2 (SEQ ID No. 1) or f16s (SEQ ID No. 2), and the other member of the pair of primers is r23s (SEQ ID No. 3) or Yer1 (SEQ ID No. 4);

(c) a Taq DNA polymerase;

(d) nucleotides dATP, dTTP, dGTP, and dCTP; and (e) a restriction enzyme selected from the group consisting of Alu I, Hae III, Mbol, Ddel, Hinfl, and a mixture thereof, for distinguishing among the species of Yersinia.

9. The kit of claim 8, further comprising a DNA template isolated from bacteria selected from the group consisting of *Escherichia coli* and a known Yersinia for positive control.

10. The kit of claim 8, wherein the buffer solution has a pH of about 8.3 and contains 10 mM Tris-HCl, 50 mM MgCl2, and 0.1% gelatin.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "OLIGODEOXYRIBONUCLEOTIDE"

( i i i ) HYPOTHETICAL: NO ( v i ) ORIGINAL SOURCE:
( A ) ORGANISM: YERSINIA ( x i ) SEQUENCE DESCRIPTION: SEQ ID NO:1:

AGAGTTTGAT CATGGCTC 18

( 2 ) INFORMATION FOR SEQ ID NO:2:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "OLIGODEOXYRIBONUCLEOTIDE"

( i i i ) HYPOTHETICAL: NO ( v i ) ORIGINAL SOURCE:
( A ) ORGANISM: YERSINIA ( x i ) SEQUENCE DESCRIPTION: SEQ ID NO:2:

TCGATGCAAC GCGAAGAA 18

( 2 ) INFORMATION FOR SEQ ID NO:3:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "OLIGODEOXYRIBONUCLEOTIDE"

( i i i ) HYPOTHETICAL: NO ( v i ) ORIGINAL SOURCE:
( A ) ORGANISM: YERSINIA

-continued ( x i ) SEQUENCE DESCRIPTION: SEQ ID NO:3:

AACGCTCCCC TACCCAAC 18

( 2 ) INFORMATION FOR SEQ ID NO:4:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "OLIGODEOXYRIBONUCLEOTIDE"

( i i i ) HYPOTHETICAL: NO ( v i ) ORIGINAL SOURCE:
( A ) ORGANISM: YERSINIA ( x i ) SEQUENCE DESCRIPTION: SEQ ID NO:4:

GTGATACGTT CGCTGCCG 18